United States Patent
Zhang et al.

(10) Patent No.: US 10,132,625 B2
(45) Date of Patent: Nov. 20, 2018

(54) METHOD FOR ACQUIRING ANISOTROPIC BASIN SURFACE ROUGHNESS AND USE THEREOF

(71) Applicant: CHINA INSTITUTE OF WATER RESOURCES AND HYDROPOWER RESEARCH, Beijing (CN)

(72) Inventors: Shaohui Zhang, Beijing (CN); Di Xu, Beijing (CN); Yinong Li, Beijing (CN); Meijian Bai, Beijing (CN); Fuxiang Li, Beijing (CN)

(73) Assignee: CHINA INSTITUTE OF WATER RESOURCES AND HYDROPOWER RESEARCH, Beijing (CN)

( * ) Notice: Subject to any disclaimer, the term of this patent is extended or adjusted under 35 U.S.C. 154(b) by 0 days.

(21) Appl. No.: 15/312,251

(22) PCT Filed: Nov. 27, 2015

(86) PCT No.: PCT/CN2015/095824
§ 371 (c)(1),
(2) Date: Nov. 18, 2016

(87) PCT Pub. No.: WO2017/088181
PCT Pub. Date: Jun. 1, 2017

(65) Prior Publication Data
US 2018/0038688 A1    Feb. 8, 2018

(51) Int. Cl.
G06F 19/00       (2018.01)
G01B 21/30       (2006.01)

(52) U.S. Cl.
CPC ................... *G01B 21/30* (2013.01)

(58) Field of Classification Search
CPC .. A63B 69/0093; A63G 31/007; E04H 4/0006
(Continued)

(56) References Cited

U.S. PATENT DOCUMENTS

2013/0061382 A1*  3/2013  Fincham ............. A63G 31/007
                                                                        4/491

FOREIGN PATENT DOCUMENTS

CN     101101612 A    1/2008
CN     101356882 A    2/2009
(Continued)

OTHER PUBLICATIONS

International Search Report dated Jun. 20, 2016.
Chinese Office Action dated Apr. 2, 2018.

*Primary Examiner* — Edward Raymond
(74) *Attorney, Agent, or Firm* — Dilworth & Barrese, LLP.; Michael J. Musella, Esq.

(57) ABSTRACT

The present invention belongs to the technical field of irrigation and water conservancy, and discloses a method for acquiring anisotropic basin surface roughness and use thereof. The method includes: preselecting two experimental strip fields respectively parallel to length direction and width direction of a target basin, to respectively acquire first surface water flow advancing process data of the two experimental strip fields, where the target basin may be regarded as a square-shaped field; acquiring two pieces of isotropic basin surface roughness respectively by using one-dimensional complete hydrodynamic model for basin irrigation according to the surface water flow advancing process data; and substituting the isotropic basin surface roughness into an elliptic equation that anisotropic basin surface roughness satisfies, to solve anisotropic basin surface roughness of the target basin, the anisotropic basin surface roughness including basin surface roughness components parallel to and perpendicular to shallow furrows on basin surface and crop planting direction in the target basin. The anisotropic basin surface roughness can truly reflect the resistance of the basin surface against the water flow, (Continued)

thereby improving simulation precision of surface irrigation hydrodynamics, and acquiring more accurate irrigation performance indexes.

11 Claims, 1 Drawing Sheet

(58) Field of Classification Search
USPC .............................. 702/33, 34, 182–185, 188
See application file for complete search history.

(56) References Cited

FOREIGN PATENT DOCUMENTS

| | | | |
|---|---|---|---|
| CN | 10319747 | A | 7/2013 |
| CN | 103197047 | A | 7/2013 |
| CN | 104677801 | A | 6/2015 |
| KR | 101396395 | B1 | 5/2014 |
| RU | 2011137609 | A | 3/2013 |
| RU | 2487530 | C2 | 7/2013 |

* cited by examiner

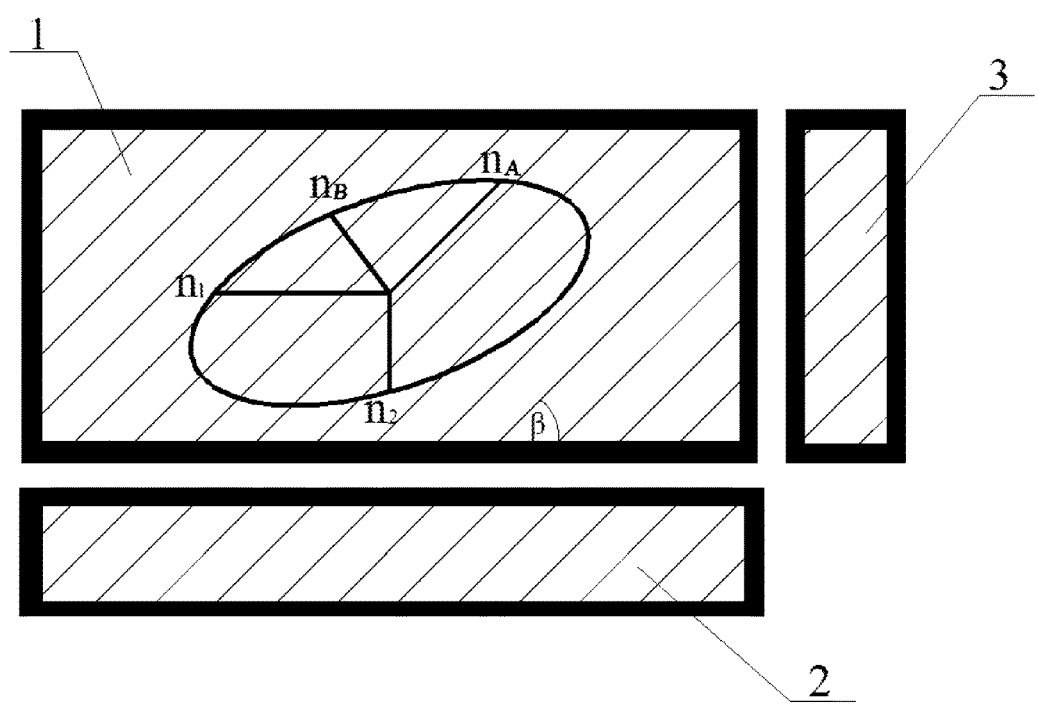

METHOD FOR ACQUIRING ANISOTROPIC BASIN SURFACE ROUGHNESS AND USE THEREOF

TECHNICAL FIELD

The present invention relates to the technical field of agricultural irrigation and water conservancy, and more particularly, to a method for acquiring anisotropic basin surface roughness and use thereof.

BACKGROUND

In analysis and evaluation of the performance of a surface irrigation system, basin surface roughness is generally adopted to represent the impact of surface resistance on surface water flow movement. Under mechanized farming and sowing conditions, the crop layout structure formed by farming and cultivation and partial unevenness of the land surface usually present specific directivity, and thus the resistance against the surface water flow passing through any spatial position of a basin has anisotropic characteristic; therefore, an anisotropic basin surface roughness model having apparent two-dimensional characteristics is required for quantitative description, to improve the simulation precision of surface water flow movement in surface irrigation, thereby improving the evaluation capability on the performance of the surface irrigation system.

The current measurement approach of anisotropic basin surface roughness is limited to a circumstance that shallow furrows on a basin surface and crops are parallel or perpendicular to ridges of basin; however, when the shallow furrows on the basin surface and the crop planting direction form a certain rotation angle with the ridges of basin, isotropic basin surface roughness having only one-dimensional characteristics is commonly measured, and is used to replace the anisotropic basin surface roughness having two-dimensional characteristics, which greatly reduces the simulation precision of a surface irrigation hydrodynamics process and further reduces the evaluation accuracy of the performance of the irrigation system.

In view of the above, in the case that the shallow furrows on the basin surface and the crop planting direction form a certain rotation angle with the ridge of basin, a method for measuring anisotropic basin surface roughness needs to be provided, and based on a mathematical tensor property of anisotropic basin surface roughness, the present invention provides a method for acquiring anisotropic basin surface roughness and use thereof, which are simple, practical, accurate and reliable.

SUMMARY

The technical problem to be solved by embodiments of the present invention is to provide a method for acquiring anisotropic basin surface roughness in a case that shallow furrows on a basin surface and crop planting direction form a certain rotation angle with ridge of basin, and use of the anisotropic basin surface roughness. The specific technical solutions are as follows:

In a first aspect, an embodiment of the present invention provides a method for acquiring anisotropic basin surface roughness, which includes: step a: preselecting a first experimental strip field parallel to length direction of a target basin, and a second experimental strip field parallel to width direction of the target basin, to respectively acquire first surface water flow advancing process data of the first experimental strip field and second surface water flow advancing process data of the second experimental strip field;

step b: acquiring first isotropic basin surface roughness and second isotropic basin surface roughness respectively by using one-dimensional complete hydrodynamic model for basin irrigation according to the first surface water flow advancing process data and the second surface water flow advancing process data; and step c: substituting the first isotropic basin surface roughness and the second isotropic basin surface roughness into an elliptic equation that anisotropic basin surface roughness satisfies, to solve anisotropic basin surface roughness of the target basin, the anisotropic basin surface roughness including basin surface roughness components parallel to and perpendicular to shallow furrows on a basin surface and crop planting direction in the target basin.

Specifically, the surface water flow advancing process data preferably includes: surface water depth, water flow advancing time in length direction of an experimental strip field, vertical uniform velocity in the length direction of the experimental strip field, unit flow rate in the length direction of the experimental strip field, basin surface relative elevation, and surface water infiltration rate.

Specifically, calculation formulas of the one-dimensional complete hydrodynamic model for basin irrigation are preferably as follows:

$$\frac{\partial h}{\partial t} + \frac{\partial q}{\partial x} = -i$$

$$\frac{\partial q}{\partial t} + \frac{\partial (qu)}{\partial x} = -gh\frac{\partial \zeta}{\partial x} - g\frac{n^2 u\sqrt{u^2+v^2}}{h^{1/3}}$$

where t is water flow advancing time in the length direction of the experimental strip field and has a unit of s; h is surface water depth and has a unit of m; u is vertical uniform velocity in the length direction of the experimental strip field and has a unit of m/s; q is unit flow rate in the length direction of the experimental strip field and has a unit of $m^3/(s \cdot m)$; g is acceleration of gravity and has a unit of $m/s^2$; $\zeta$ is surface water level relative elevation, $\zeta$=surface water depth+basin surface relative elevation, and has a unit of m; n is isotropic basin surface roughness and has a unit of $s/m^{1/3}$; and i is surface water infiltration rate and has a unit of m/s.

Specifically, the elliptic equation is preferably as follows:

$$\frac{x_n^2}{n_B^2} + \frac{y_n^2}{n_A^2} = 1$$

where $n_A$ is a basin surface roughness component parallel to the shallow furrows on the basin surface and the crop planting direction in the target basin; and $n_B$ is a basin surface roughness component perpendicular to the shallow furrows on the basin surface and the crop planting direction in the target basin.

In a second aspect, an embodiment of the present invention provides use of the anisotropic basin surface roughness obtained by using the above method in a surface irrigation process.

Specifically, the use preferably includes: determining simulation precision of the anisotropic basin surface roughness, and applying the anisotropic basin surface roughness to a two-dimensional complete hydrodynamic model for basin irrigation, to analyze and evaluate the irrigation performance of the target basin.

Specifically, the determining the simulation precision of the anisotropic basin surface roughness preferably includes:

step α: substituting the anisotropic basin surface roughness into the two-dimensional complete hydrodynamic model for basin irrigation, to acquire a simulated value of the surface water flow advancing process data based on the anisotropic basin surface roughness; meanwhile, substituting the isotropic basin surface roughness based on the target basin into the two-dimensional complete hydrodynamic model for basin irrigation, to acquire simulated value of the surface water flow advancing process data based on the isotropic basin surface roughness;

step β: calculating a first average relative error between the simulated value of the surface water flow advancing process data based on the anisotropic basin surface roughness and an actually measured value of the surface water flow advancing process data; meanwhile, calculating a second average relative error between the simulated value of the surface water flow advancing process data based on the isotropic basin surface roughness and the actually measured value of the surface water flow advancing process data; and step γ: determining simulation precision of the anisotropic basin surface roughness according to the first average relative error and the second average relative error.

Specifically, calculation formulas of the two-dimensional complete hydrodynamic model for basin irrigation are preferably as follows:

$$\frac{\partial h}{\partial t}+\frac{\partial q}{\partial x}+\frac{\partial p}{\partial y}=-i$$

$$\frac{\partial q}{\partial t}+\frac{\partial (qu)}{\partial x}+\frac{\partial (qv)}{\partial y}=$$
$$-gh\frac{\partial \zeta}{\partial x}-g\frac{\sqrt{u^2+v^2}}{h^{1/3}}[u(n_A^2-n_B^2)\sin\beta\cos\beta+v(n_A^2\sin^2\beta+n_B^2\cos^2\beta)]$$

$$\frac{\partial p}{\partial t}+\frac{\partial (pu)}{\partial x}+\frac{\partial (pv)}{\partial y}=$$
$$-gh\frac{\partial \zeta}{\partial y}-g\frac{\sqrt{u^2+v^2}}{h^{1/3}}[u(n_A^2-n_B^2)\sin\beta\cos\beta+v(n_A^2\sin^2\beta+n_B^2\cos^2\beta)]$$

where t is water flow advancing time and has a unit of s; h is surface water depth and has a unit of m; u and v are vertical uniform velocities in x-coordinate direction and y-coordinate direction and have a unit of m/s, respectively; q and p are unit flow rates in the x-coordinate direction and the y-coordinate direction and have a unit of $m^3/(s\cdot m)$, respectively; g is acceleration of gravity and has a unit of $m/s^2$; ζ is surface water level relative elevation, ζ=surface water depth+basin surface relative elevation, and has a unit of m; $n_A$ is basin surface roughness component parallel to the shallow furrows on the basin surface and the crop planting direction in the target basin, and has a unit of $s/m^{1/3}$; $n_B$ is basin surface roughness component perpendicular to the shallow furrows on the basin surface and the crop planting direction in the target basin, and has a unit of $s/m^{1/3}$; i is surface water infiltration rate and has a unit of m/s; and β is an angle formed by the shallow furrows on the basin surface and the crop planting direction with the x-coordinate direction.

The technical solutions provided by the embodiments of the present invention have the following beneficial effects:

In the method for acquiring anisotropic basin surface roughness provided by the embodiment of the present invention, the two experimental strip fields are selected according to orientational arrangement of the target basin, and thus the one-dimensional isotropic basin surface roughness of the two experimental strip fields is acquired, and the two-dimensional anisotropic basin surface roughness which corresponds to the shallow furrows on the basin surface and the crop planting direction form a random rotation angle with the ridge of basin may be calculated by using the elliptic equation that the anisotropic basin surface roughness satisfies and based on a mathematical tensor property of the anisotropic basin surface roughness. The two-dimensional anisotropic basin surface roughness can more truly reflect the resistance of the basin surface against the water flow, thereby improving simulation precision of surface irrigation hydrodynamics (also understood as basin irrigation hydrodynamics), and acquiring more accurate irrigation performance indexes. Therefore, the method for acquiring anisotropic basin surface roughness provided by the embodiment of the present invention is not only simple and practical, but also accurate and reliable.

BRIEF DESCRIPTION OF THE DRAWINGS

To illustrate the technical solutions in the embodiments of the present invention more clearly, the accompanying drawings required for describing the embodiments are introduced briefly in the following. Apparently, the accompanying drawings in the following description are only some embodiments of the present invention, and persons of ordinary skill in the art can derive other drawings from the accompanying drawings without creative efforts.

FIG. 1 is a schematic diagram illustrating position relationships between a first experimental strip field, a second experimental strip field and a target basin according to an embodiment of the present invention.

LIST OF REFERENCE NUMERALS 1 target basin
2 first experimental strip field
3 second experimental strip field
$n_1$ first isotropic basin surface roughness based on the first experimental strip field
$n_2$ second isotropic basin surface roughness based on the second experimental strip field
$n_A$ basin surface roughness component of anisotropic basin surface roughness parallel to shallow furrows on a basin surface and a crop planting direction in the target basin
$n_B$ basin surface roughness component of anisotropic basin surface roughness perpendicular to the shallow furrows on the basin surface and the crop planting direction in the target basin
β angle formed by the shallow furrows on the basin surface and the crop planting direction with an x-coordinate direction

DETAILED DESCRIPTION

To make the objectives, technical solutions and advantages of the present invention clearer, the embodiments of the present invention are further described in detail below with reference to the accompanying drawings.

In a first aspect, an embodiment of the present invention provides a method for acquiring anisotropic basin surface roughness, which includes the following steps:

step 101: preselect a first experimental strip field 2 parallel to length direction of a target basin 1, and a second experimental strip field 3 parallel to width direction of the target basin 1, to respectively acquire first surface water flow advancing process data of the first experimental strip field 2 and second surface water flow advancing process data of the second experimental strip field 3, where the target basin 1 may be regarded as a square-shaped field;

step 102: acquire first isotropic basin surface roughness and second isotropic basin surface roughness respectively by using one-dimensional complete hydrodynamic model for basin irrigation according to the first surface water flow advancing process data and the second surface water flow advancing process data; and step 103: substitute the first isotropic basin surface roughness and the second isotropic basin surface roughness into an elliptic equation that anisotropic basin surface roughness satisfies, to solve anisotropic basin surface roughness of the target basin 1, the anisotropic basin surface roughness including basin surface roughness components parallel to and perpendicular to shallow furrows on a basin surface and a crop planting direction in the target basin 1.

Position relationships between the first experimental strip field 2, the second experimental strip field 3 and the target basin 1, and an ellipse formed by the first isotropic basin surface roughness obtained from the first experimental strip field 2, the second isotropic basin surface roughness obtained from the second experimental strip field 3, and the anisotropic basin surface roughness based on the target basin 1 is shown in FIG. 1. It can be seen from FIG. 1 that, the length direction of the first experimental strip field 2 is parallel to the length direction of the target basin 1, the length direction of the second experimental strip field 3 is parallel to the width direction of the target basin 1, and it is ensured that the shallow furrows on the basin surface and the crop planting direction in the first experimental strip field 2 and the second experimental strip field 3 are all identical to the shallow furrows on the basin surface and the crop planting direction in the target basin 1. $n_1$ in the ellipse represents the first isotropic basin surface roughness obtained based on the first surface water flow advancing process data in the first experimental strip field 2, $n_2$ in the ellipse represents the second isotropic basin surface roughness obtained based on the second surface water flow advancing process data in the second experimental strip field 3, $n_A$ in the ellipse represents the basin surface roughness component of the anisotropic basin surface roughness parallel to the shallow furrows on the basin surface and the crop planting direction in the target basin 1; and $n_B$ in the ellipse represents the basin surface roughness component of the anisotropic basin surface roughness perpendicular to the shallow furrows on the basin surface and the crop planting direction in the target basin 1.

In the method for acquiring anisotropic basin surface roughness provided by the embodiment of the present invention, the first experimental strip field 2 and the second experimental strip field 3 are selected according to orientational arrangement of the target basin 1, and thus the one-dimensional isotropic basin surface roughness of the two experimental strip fields is acquired, and the two-dimensional anisotropic basin surface roughness which corresponds to the shallow furrows on the basin surface and the crop planting direction form a random rotation angle with the ridge of basin may be calculated by using the elliptic equation that the anisotropic basin surface roughness satisfies and based on a mathematical tensor property of the anisotropic basin surface roughness. The two-dimensional anisotropic basin surface roughness can more truly reflect the resistance of the basin land surface against the water flow, thereby improving simulation precision of surface irrigation hydrodynamics (also understood as basin irrigation hydrodynamics), and acquiring more accurate irrigation performance indexes. Therefore, the method for acquiring anisotropic basin surface roughness provided by the embodiment of the present invention is not only simple and practical, but also accurate and reliable.

Specifically, data information included in the first surface water flow advancing process data and the second surface water flow advancing process data should be of the same type, and specifically includes surface water depth, water flow advancing time in the length direction of the experimental strip field which can actually be measured, and vertical uniform velocity in the length direction of the experimental strip field, unit flow rate in the length direction of the experimental strip field, basin surface relative elevation, and surface water infiltration rate, where basin surface relative elevation refers to a relative value of basin surface elevation. It can be understood that, acquiring the surface water flow advancing process data belongs to the prior art, and a specific process of acquiring the surface water flow advancing process data is not limited in the embodiment of the present invention.

Further, the first isotropic basin surface roughness $n_1$ and the second isotropic basin surface roughness $n_2$ are respectively acquired by using the one-dimensional complete hydrodynamic model for basin irrigation based on the first surface water flow advancing process data and the second surface water flow advancing process data, where calculation formulas of the one-dimensional complete hydrodynamic model for basin irrigation are as follows:

$$\frac{\partial h}{\partial t} + \frac{\partial q}{\partial x} = -i$$

$$\frac{\partial q}{\partial t} + \frac{\partial (qu)}{\partial x} = -gh\frac{\partial \zeta}{\partial x} - g\frac{n^2 u\sqrt{u^2+v^2}}{h^{1/3}}$$

where t is the water flow advancing time and is calculated in s; h is the surface water depth and is calculated in m; u is the vertical uniform velocity in the length direction of the experimental strip field and is calculated in m/s; q is the unit flow rate in the length direction of the experimental strip field and is calculated in m$^3$/(s·m); g is acceleration of gravity and is calculated in m/s$^2$; $\zeta$ is surface water level relative elevation, $\zeta$=surface water depth+basin surface relative elevation, and is calculated in m; n is isotropic basin surface roughness and is calculated in s/m$^{1/3}$; and i is surface water infiltration rate and is calculated in (m/s).

Further, the elliptic equation applied in the process of solving the anisotropic basin surface roughness of the target basin 1 is as follows:

$$\frac{x_n^2}{n_B^2} + \frac{y_n^2}{n_A^2} = 1$$

where $n_A$ is a basin surface roughness component parallel to the shallow furrows on the basin surface and the crop planting direction in the target basin 1; and $n_B$ is a basin surface roughness component perpendicular to the shallow furrows on the basin surface and the crop planting direction in the target basin 1. The first isotropic basin surface roughness $n_1$ has corresponding components $x_1$ and $y_1$ in an x-coordinate direction and a y-coordinate direction; correspondingly, the second isotropic basin surface roughness $n_2$ has corresponding components $x_2$ and $y_2$ in the x-coordinate direction and the y-coordinate direction, and because $x_1$, $y_1$, $x_2$ and $y_2$ are all given values, the values of $n_A$ and $n_B$ can be easily acquired accordingly, as a result, anisotropic basin surface roughness is acquired.

On the basis of the anisotropic basin surface roughness of the target basin 1 acquired by using the above method, in a second aspect, an embodiment of the present invention provides use of the anisotropic basin surface roughness in surface irrigation process.

Specifically, the use includes: determining simulation precision of the anisotropic basin surface roughness, and applying the anisotropic basin surface roughness to a two-dimensional hydrodynamic ridge irrigation model, to analyze and evaluate the irrigation performance of the target basin 1.

Specifically, the determining the simulation precision of the anisotropic basin surface roughness includes the following steps:

step 201: substituting the anisotropic basin surface roughness into the two-dimensional complete hydrodynamic model for basin irrigation, to acquire a simulated value of surface water flow advancing process data based on the anisotropic basin surface roughness; meanwhile, substitute the isotropic basin surface roughness based on the target basin 1 into the two-dimensional complete hydrodynamic model for basin irrigation, to acquire a simulated value of the surface water flow advancing process data based on the isotropic basin surface roughness. where the isotropic basin surface roughness based on the target basin 1 can be acquired by using a method provided in the prior art, so the acquiring process for the isotropic basin surface roughness is not further specifically limited in the embodiment of the present invention.

step 202: calculating a first average relative error between the simulated value of the surface water flow advancing process data based on the anisotropic basin surface roughness and an actually measured value of the surface water flow advancing process data; meanwhile, calculating a second average relative error between the simulated value of the surface water flow advancing process data based on the isotropic basin surface roughness and the actually measured value of the surface water flow advancing process data. where the surface water flow advancing process data in step 201 and step 202 is preferably water flow advancing time; and step 203: determining simulation precision of the anisotropic basin surface roughness according to the first average relative error and the second average relative error.

Calculation formulas of the two-dimensional complete hydrodynamic model for basin irrigation in step 201 are as follows:

$$\frac{\partial h}{\partial t} + \frac{\partial q}{\partial x} + \frac{\partial p}{\partial y} = -i$$

$$\frac{\partial q}{\partial t} + \frac{\partial (qu)}{\partial x} + \frac{\partial (qv)}{\partial y} =$$

$$-gh\frac{\partial \zeta}{\partial x} - g\frac{\sqrt{u^2+v^2}}{h^{1/3}}[u(n_A^2 - n_B^2)\sin\beta\cos\beta + v(n_A^2 \sin^2\beta + n_B^2 \cos^2\beta)]$$

$$\frac{\partial p}{\partial t} + \frac{\partial (pu)}{\partial x} + \frac{\partial (pv)}{\partial y} =$$

$$-gh\frac{\partial \zeta}{\partial y} - g\frac{\sqrt{u^2+v^2}}{h^{1/3}}[u(n_A^2 - n_B^2)\sin\beta\cos\beta + v(n_A^2 \sin^2\beta + n_B^2 \cos^2\beta)]$$

where t is water flow advancing time and has a unit of s; h is surface water depth and has a unit of m; u and v are vertical uniform velocities in an x-coordinate direction and a y-coordinate direction and have a unit of m/s, respectively; q and p are unit flow rates in the x-coordinate direction and the y-coordinate direction and have a unit of m³/(s·m), respectively; g is acceleration of gravity and has a unit of m/s²; $\zeta$ is surface water level relative elevation, $\zeta$=surface water depth+surface relative elevation, and has a unit of m; $n_A$ is a basin surface roughness component parallel to the shallow furrows on the basin surface and the crop planting direction in the target basin, and has a unit of s/m$^{1/3}$; $n_B$ is a basin surface roughness component perpendicular to the shallow furrows on the basin surface and the crop planting direction in the target basin 1, and has a unit of s/m$^{1/3}$; i is surface water infiltration rate and has a unit of m/s; and β is an angle formed by the shallow furrows on the basin surface and the crop planting direction with the x-coordinate direction, and the x-coordinate direction and the y-coordinate direction respectively referring to length direction and width direction of the target basin.

Persons skilled in the art can understand that, as a way of implementation, the calculation of the one-dimensional complete hydrodynamic model for basin irrigation and the two-dimensional complete hydrodynamic model for basin irrigation can be implemented by creating a corresponding mathematical model in a computer.

Further, in step 202, the average relative error can be calculated by using the following calculation formula:

$$ARE = \sum_{i=1}^{M} \frac{|t_i^o - t_i^s|}{t_i^o}$$

where $t_i^o$ and $t_i^s$ are respectively actually measured water flow advancing time and simulated time calculated by using the two-dimensional complete hydrodynamic model for basin irrigation when the surface water flow advances to an $i^{th}$ measure point in the basin, and have a unit of min; and M is the number of measure points in the basin.

The present invention is further described below through specific embodiments.

Embodiment 1

The anisotropic basin surface roughness of three basins in the district of a regiment of Xinjiang Production and Construction Corps is acquired in this embodiment. The three basins are respectively numbered as #1, #2, #3 in order, where Table 1 shows geometric dimensions of the three basin and the isotropic basin surface roughness based on the three basin that is acquired by using the prior art. Table 1 is specifically as follows:

TABLE 1

| Basin No. | Geometric dimensions of basin (m × m) | Isotropic basin surface roughness (s/m$^{1/3}$) |
| --- | --- | --- |
| #1 | 80 × 50 | 0.08 |
| #2 | 100 × 60 | 0.12 |
| #3 | 200 × 50 | 0.09 |

Then, the anisotropic basin surface roughness of the three basin is acquired by using the method according to the embodiment of the present invention, and the specific steps are as follows:

step 1: set a first experimental strip field and a second experimental strip field parallel to length direction and width direction of a target basin with random shallow furrows on a basin surface and a random crop planting direction, respectively; observe surface water flow advancing process data in the two experimental strip fields; and acquire first isotropic basin surface roughness $n_1$ and second isotropic basin surface roughness $n_2$ by using one-dimensional complete hydrodynamic model for basin irrigation based on the two sets of surface water flow advancing data of the two experimental strip fields.

step 2: according to the principle for solving a binary quadratic equation, substitute $n_1$ and $n_2$ into an elliptic equation that anisotropic basin surface roughness satisfies, to acquire a basin surface roughness component $n_A$ of the anisotropic basin surface roughness parallel to the shallow furrows on the basin surface and the crop planting direction in the target basin and a basin surface roughness component $n_B$ of the anisotropic basin surface roughness perpendicular to the shallow furrows on the basin surface and the crop planting direction in the target basin, wherein the specific result is Shown in Table 2:

TABLE 2

| | Anisotropic basin surface roughness (s/m$^{1/3}$) | |
|---|---|---|
| Basin No. | $n_A$ | $n_B$ |
| #1 | 0.06 | 0.1 |
| #2 | 0.08 | 0.15 |
| #3 | 0.07 | 0.13 | step 3: substitute the acquired $n_A$ and $n_B$ into two-dimensional complete hydrodynamic model for basin irrigation, to acquire a simulated value of surface water flow advancing time based on the anisotropic basin surface roughness; meanwhile, substitute the isotropic basin surface roughness in Table 1 correspondingly into the two-dimensional complete hydrodynamic model for basin irrigation, to acquire a simulated value of the surface water flow advancing time based on the isotropic basin surface roughness; and step 4: calculate a first average relative error between the simulated value of the surface water flow advancing time based on the anisotropic basin surface roughness and an actually measured value of the surface water flow advancing time; meanwhile, calculate a second average relative error between the simulated value of the surface water flow advancing time based on the isotropic basin surface roughness and the actually measured value of the surface water flow advancing time, to quantitatively compare simulation precision for the anisotropic basin surface roughness with simulation precision for the isotropic basin surface roughness, wherein the result is shown in Table 3:

TABLE 3

| Basin No. | First average relative error | Second average relative error |
|---|---|---|
| #1 | 5.2% | 15.5% |
| #2 | 6.1% | 13.9% |
| #3 | 4.2% | 11.3% |

It can be seen from Table 3 that, the simulation precision of the two-dimensional complete hydrodynamic basin irrigation model is significantly improved after the anisotropic basin surface roughness is adopted.

Further, step 4 is performed in this embodiment, that is, calculate simulated values of irrigation performance indexes of each basin according to the acquired simulated value of the surface water flow advancing process data based on the anisotropic basin surface roughness and the acquired simulated value of the surface water flow advancing process data based on the isotropic basin surface roughness, where the irrigation performance indexes include irrigation uniformity Ea and water storage efficiency CU, and calculation formulas of Ea and CU are respectively as follows:

$$E_a = \frac{Z_s}{Z_{avg}}$$

$$CU = 1 - \frac{\sum_{i=1}^{n} |Z_i - Z_{avg}|}{n \cdot Z_{avg}}$$

where $$Z_{avg} = \frac{\sum_{i=1}^{n} kt^\alpha}{n}$$

is average water irrigation depth and has a unit of m;

$$Z_s = \frac{\sum_{i=1}^{n} Z_{avg}}{n}$$

is average water depth stored in a crop root zone after irrigation and has a unit of m, when $Z_{avg} \geq 0.08$ m, $Z_{avg}$ is 0.08 m, and when $Z_{avg} < 0.08$ m, an actual value of $Z_{avg}$ is adopted; $Z_i$ is water irrigation depth at an $i^{th}$ node, and $Z_i = kt^\alpha$; n is the number of nodes in the basin; t is water flow advancing time; k and $\alpha$ are both soil infiltration parameters acquired by actual measurement.

The test result is shown in Table 4:

TABLE 4

| | Simulated values of irrigation performance indexes based on anisotropic basin surface roughness | | Simulated values of irrigation performance indexes based on isotropic basin surface roughness | |
|---|---|---|---|---|
| Basin No. | $E_a$ | CU | $E_a$ | CU |
| #1 | 0.92 | 0.86 | 0.83 | 0.76 |
| #2 | 0.86 | 0.85 | 0.76 | 0.74 |
| #3 | 0.91 | 0.78 | 0.81 | 0.67 |

It can be seen from Table 4 that, the difference between the simulated values of the irrigation performance indexes based on the anisotropic basin surface roughness and the simulated values of the irrigation performance indexes based on the isotropic basin surface roughness is large. It can be seen from the data in Table 3 that, the simulated values of the irrigation performance indexes based on the anisotropic basin surface roughness are closer to physical facts. Therefore, the anisotropic basin surface roughness obtained by using the method provided by the embodiment of the present invention can effectively improve simulation precision of irrigation hydrodynamics and irrigation performance evaluation and analysis capabilities.

The above descriptions are merely preferred embodiments of the present invention, but not intended to limit the present invention. Any modification, equivalent replacement, and improvement made without departing from the spirit and principle of the present invention shall fall within the protection scope of the present invention.

The invention claimed is:

1. A method for acquiring anisotropic basin surface roughness implemented by a computer, comprising: step a: preselecting a first experimental strip field parallel to a length direction of a target basin, and a second experimental strip field parallel to a width direction of the target basin, to respectively acquire first surface water flow advancing process data of the first experimental strip field and second surface water flow advancing process data of the second experimental strip field;

step b: acquiring first isotropic basin surface roughness and second isotropic basin surface roughness respectively by using one-dimensional complete hydrodynamic model for basin irrigation according to the first surface water flow advancing process data and the second surface water flow advancing process data; and step c: substituting the first isotropic basin surface roughness and the second isotropic basin surface roughness into an elliptic equation that anisotropic basin surface roughness satisfies, to solve anisotropic basin surface roughness of the target basin, the anisotropic basin surface roughness including basin surface roughness components parallel to and perpendicular to shallow furrows on a basin surface and crop planting direction in the target basin;

wherein, the anisotropic basin surface roughness of the target basin is used for water allocation of the target basin when surface irrigation for the target basin is conducted.

2. The acquiring method according to claim 1, wherein the surface water flow advancing process data comprises: surface water depth, water flow advancing time in length direction of an experimental strip field, vertical uniform velocity in the length direction of the experimental strip field, unit flow rate in the length direction of the experimental strip field, basin surface relative elevation, and surface water infiltration rate.

3. The acquiring method according to claim 2, wherein calculation formulas of the one-dimensional complete hydrodynamic model for basin irrigation are as follows:

$$\frac{\partial h}{\partial t} + \frac{\partial q}{\partial x} = -i$$

$$\frac{\partial q}{\partial t} + \frac{\partial (qu)}{\partial x} = -gh\frac{\partial \zeta}{\partial x} - g\frac{n^2 u \sqrt{u^2+v^2}}{h^{1/3}}$$

where t is water flow advancing time in the length direction of the experimental strip field and has a unit of s; h is surface water depth and has a unit of m; u is vertical uniform velocity in the length direction of the experimental strip field and has a unit of m/s; q is unit flow rate in the length direction of the experimental strip field and has a unit of m³/(s·m); g is acceleration of gravity and has a unit of m/s²; ζ is surface water level relative elevation, ζ= surface water depth +surface relative elevation, and has a unit of m; n is isotropic basin surface roughness and has a unit of $s/m^{1/13}$; and i is surface water infiltration rate and has a unit of m/s.

4. The acquiring method according to claim 3, wherein the elliptic equation is as follows:

$$\frac{x_n^2}{n_B^2} + \frac{y_n^2}{n_A^2} = 1$$

where $n_A$ is a basin surface roughness component parallel to the shallow furrows on the basin surface and the crop planting direction in the target basin; and $n_B$ is a basin surface roughness component perpendicular to the shallow furrows on the basin surface and the crop planting direction in the target basin.

5. Use of the anisotropic basin surface roughness obtained by using the method according to claim 1 in a surface irrigation process.

6. The use according to claim 5, comprising: determining simulation precision of the anisotropic basin surface roughness, and applying the anisotropic basin surface roughness to a two-dimensional complete hydrodynamic model for basin irrigation, to analyze and evaluate the irrigation performance of the target basin.

7. The use according to claim 6, wherein the determining the simulation precision of the anisotropic basin surface roughness comprises:

step α: substituting the anisotropic basin surface roughness into the two-dimensional complete hydrodynamic model for basin irrigation, to acquire a simulated value of the surface water flow advancing process data based on the anisotropic basin surface roughness; meanwhile, substituting the isotropic basin surface roughness based on the target basin into the two-dimensional complete hydrodynamic model for basin irrigation, to acquire a simulated value of the surface water flow advancing process data based on the isotropic basin surface roughness;

step β: calculating a first average relative error between the simulated value of the surface water flow advancing process data based on the anisotropic basin surface roughness arid an actually measured value of the surface water flow advancing process data; meanwhile, calculating a second average relative error between the simulated value of the surface water flow advancing process data based on the isotropic basin surface roughness and the actually measured value of the surface water flow advancing process data; and step γ: determining simulation precision of the anisotropic basin surface roughness according to the first average relative error and the second average relative error.

8. The use according to claim 7, wherein calculation formulas of the two-dimensional complete hydrodynamic model for basin irrigation are as follows:

$$\frac{\partial h}{\partial t} + \frac{\partial q}{\partial x} + \frac{\partial p}{\partial y} = -i$$

$$\frac{\partial q}{\partial t} + \frac{\partial (qu)}{\partial x} + \frac{\partial (qv)}{\partial y} =$$

$$-gh\frac{\partial \zeta}{\partial x} - g\frac{\sqrt{u^2+v^2}}{h^{1/3}}[u(n_A^2 - n_B^2)\sin\beta\cos\beta + v(n_A^2 \sin^2\beta + n_B^2 \cos^2\beta)]$$

-continued $$\frac{\partial p}{\partial t} + \frac{\partial(pu)}{\partial x} + \frac{\partial(pv)}{\partial y} =$$
$$-gh\frac{\partial \zeta}{\partial y} - g\frac{\sqrt{u^2+v^2}}{h^{1/3}}[u(n_A^2 - n_B^2)\sin\beta\cos\beta + v(n_A^2\sin^2\beta + n_B^2\cos^2\beta)] \quad 5$$

where t is water flow advancing time and has a unit of s; h is surface water depth and has a unit of m; u and v are vertical uniform velocities in x-coordinate direction and y-coordinate direction and have a unit of m/s, respectively; q and p are unit flow rates in the x-coordinate direction and the y-coordinate direction and have a unit of m $^3$(s·m), respectively; g is acceleration of gravity and has a unit of m/s$^2$; $\zeta$ is surface water level relative elevation, $\zeta$=surface water depth +surface relative elevation, and is calculated in m; $n_A$ is basin surface roughness component parallel to the shallow furrows on the basin surface and the crop planting direction in the target basin, and has a unit of s/m$^{1/3}$; $n_B$ is basin surface roughness component perpendicular to the shallow furrows on the basin surface and the crop planting direction in the target basin, and has a unit of s/m$^{1/3}$; i is surface water infiltration rate and has a unit of m/s; and β is an angle formed by the shallow furrows on the basin surface and the crop planting direction with the x-coordinate direction.

9. Use of the anisotropic basin surface roughness obtained by using the method according to claim 2 in a surface irrigation process.

10. Use of the anisotropic basin surface roughness obtained by using the method according to claim 3 in a surface irrigation process.

11. Use of the anisotropic basin surface roughness obtained by using the method according to claim 4 in a surface irrigation process.

* * * * *